(12) United States Patent
Ramakrishna et al.

(10) Patent No.: US 6,420,146 B1
(45) Date of Patent: Jul. 16, 2002

(54) PROCESS FOR THE PREPARATION OF STABLE YEAST CRYSTALS FOR ENHANCED PRODUCTION OF ETHANOL

(75) Inventors: Sonti Venkata Ramakrishna; Reddy Shetty Prakasham; Palle Komaraiah, all of Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/538,181

(22) Filed: Mar. 30, 2000

(51) Int. Cl.$^7$ .............................. C12P 7/14; C12P 7/06; C12N 11/02; C12N 1/36; A23C 9/12
(52) U.S. Cl. ........................ 435/162; 435/161; 435/177; 435/243; 426/62
(58) Field of Search .................. 435/161, 162, 435/177, 243; 426/62

(56) References Cited

U.S. PATENT DOCUMENTS 5,697,186 A  *  12/1997  Neyra et al. ................. 47/57.6
5,869,117 A  *  2/1999  Neufeld et al. ............... 426/11
6,015,699 A  *  1/2000  Patil et al. ................... 435/161

OTHER PUBLICATIONS

Paul J. Cano an Jamie S. Colome, Microbiology, p. 798, Jan. 1986.*

* cited by examiner

Primary Examiner—Christopher R. Tate
Assistant Examiner—Randall Winston
(74) Attorney, Agent, or Firm—Lackenbach Siegel; J. Harold Nissen

(57) ABSTRACT

The invention provides a process for the preparation of stable yeast crystals for enhanced production of ethanol, said process comprising the steps of culturing yeast Sacchromyces spp. in a growth medium, obtaining immobilized yeast heads, separating and dehydrating the stable yeast crystals, adding the stable yeast crystals to a 5–8% molasses solution and incubating the said crystals for a period ranging between 6–48 hours at a temperature ranging between 24–32° C. to obtain activated stable yeast heads to obtain crystals which are separated in a fermentation broth containing molasses and having a total reducing sugar concentration in the range of 10–30% and recovering the ethanol from the fermentation broth by known methods.

16 Claims, No Drawings

PROCESS FOR THE PREPARATION OF STABLE YEAST CRYSTALS FOR ENHANCED PRODUCTION OF ETHANOL

FIELD OF THE INVENTION

This invention relates to an improved process for the preparation of stable yeast crystals and a process for the enhanced production of ethanol using the said stable yeast crystals. This invention, particularly, relates to a process for the preparation of stable yeast crystals and production of ethanol using these crystals, which has wide industrial application as solvent, food, medicine and intermediate for synthesis of variety of organic compounds.

BACKGROUND OF INVENTION

The demand for ethanol is ever increasing mainly due to the rapid industrialization and fast population growth, which resulted in renewed interest in the development of suitable fermentation processes for ethanol production. Even today, ethanol production is carried out by conventional batch fermentation techniques using *Sachhromyces cereviceae* cultures. This method of ethanol fermentation with yeast cultures requires maintenance of yeast cultures and pitching of yeast for every batch. Hitherto several attempts have been made to enhance the ethanol production with free and immobilized yeast cells. The ethanol fermentations are generally carried out using *Sacchromyces cereviceae* in diluted molasses solutions in a batch reactor for a period of 24–48 hours [S. V. Ramakrishna, V. P. Sreedharan and P. Prema. In *Bioreactor Immobilized Enzymes and Cells: Fundamentals and Applications* (Ed MoodYoung), Elsevier *Appl. Sci.*, Amsterdam, 1988, 251–260]. The major disadvantages of the batch process are its low productivity, extremely slow and inefficient, higher operating as well as capital investment [D. Das. R. G. Nandkishor, K. Murali and P. S. Gupta *J. Ferment.Bioengg.* 1993, 75, 132–137: D. Weuster-Botz *Appl. Microbiol. Biotechnol,* 1993, 39, 679–684]. Many alternative fermentation strategies such as high cell densities in the fermentor, larger throughput by continuous mode of operation using cell recycle [C. W. Lee and H. N. Chang *Biotehcnol. Bioengg,* 1987, 29, 1105–1112], extractive fermentation [M. Minier and G. Goma Biotehcnol. Bioengg. 1982, 24, 1565–1579] and whole cell immobilization by various techniques [S. V. Ramakrishna and R. S. Prakasham *Current Science,* 1999, 77, 87–100] have been attempted to enhance volumetric productivity of the system. But these methodologies suffer from the drawback that the yeast cells has to be added in every batch. Continuous fermentation with cell recycles [T. K. Ghosh and R. D. Tyagi *Biotechnol. Bioengg,* 1979, 21; 1387; G. H. Gil, W. J. Jones and T. G. Tomabene *Enzyme Microb. Technol.,* 1991, 13; 390] and vacuume fermentation [G. R. Cysewski and C. R. Wilke *Biotechnol, Bioengg,* 1977, 19; 1125] have resulted in considerable increase in the productivity. However, the cell recycling system involves considerable cost input for separation of yeast cells from the fermented broth. One of the attractive alternate method received wide attention is the high cell density fermentations. In this regard the reuse of immobilized yeast cells, instead of free cells, has been attempted by several researchers [R. Jamuna and S. V. Ramakrishna *Biomass Bioenergy,* 1992, 3; 117–119]. Many methods of cell immobilization such as absorption on solid matrices, cross-linking covalent bonding and entrapment have been tried [S. V. Ramakrishna and R. S. Prakasham *Curr. Sci.,* 1999, 77; 87–100] using natural polymers such as agar, agarose, alginates & carageenan and synthetic polymers like polyacrylamide, poly vinyl alcohol have been used for entrapment [S. V. Ramakrishna and R. S. Prakasham *Curr. Sci.,* 1999, 77; 87–100]. Due to toxicity problems, the synthetic polymers have been found to have limited use. One of the major limitation with entrapped cells in natural polymers is its low mechanical strength and its density due to which the entrapped particles tends to float, causing serious engineering problems both in packed and fluidized bed reactor. Recently, T. E. Abraham et all (1990) have developed high density gel beads by incorporating dense inert compounds [T. E. Abraham, J. Rajagopalan, S. V. Ramakrishna and A. D. Damadaran, Indian Patent, 761/DEL/90]. However, the resultant gel beads with improved density were found to have lower mechanical strength due to weak ionic bonds of the polymeric network. There is not report available production of stable immobilized yeast beads. Various types of reactor configurations have been attempted to produce ethanol with entrapped cells [F. Godia, C. Casad, and C. Sola *Process Biochem,* 1987, 43–48]. One of the major limitation with entrapped cells is that the gas generated during fermentation get entrapped in the gel particles which in turn lowers the density disintegrates the beads [S. V. Ramakrishna, V. P. Sreedharan and P. Prema. In: *Bioreactor Immobilized Enzymes and Cells: Fundamentals and Applications* (Ed MoodYoung), Elsevier *Appl. Sci.,* Amsterdam, 1988, 251–260].

OBJECTIVES OF THE INVENTION

The first objective of the present invention is to provide an improved process for the preparation of stable yeast crystals.

The second objective of the present invention is the use of the stable yeast crystals prepared by the process of present invention for enhanced production of ethanol.

The third objective of the present invention is to store the stable yeast crystals at room temperature without loosing its activity.

The fourth objective of the present invention is to provide an easy transportation of stable yeast crystals.

The fifth objective of the present invention is to provide stable yeast crystals for repeated use.

The sixth objective of this invention is to provide cost effective improved alcohol fermentation.

The seventh objective of the present invention is to reduce the product inhibition during ethanol fermentation.

The eighth objective of the present invention is to provide an easy process of ethanol production.

The ninth objective of the present invention is to enhance the rate of ethanol fermentation.

SUMMARY OF THE INVENTION

The novelty lies in the present invention is the preparation of novel stable yeast crystals which are mechanically strong and biologically active, they can be employed either in stirred tank reactors or in fluidized beds in batch or continuous fermentations, for enhanced ethanol production. The gas generation during fermentation does not lower its density nor weaken the integrity of the matrix.

DETAILED DESCRIPTION OF THE INVENTION

Accordingly, the present invention provides an improved process for the preparation of stable yeast crystals for enhanced production of ethanol which comprises culturing of yeast (*Sacchromyces cereviceae*) in a conventional growth medium, separating the yeast, immobilization of yeast using aqueous natural polymer solution by known methods to obtain immobilized yeast beads, separation of the said immobilized yeast beads and dehydration at the temperature in the range of 24–36° C. for a period of 2–20 hours to obtain stable yeast crystals having the moisture content in the range between 5–30%, adding novel stable yeast crystals to 5–8% molasses solution and incubating the said crystals for a period ranging between 6–48 hours at a temperature ranging between 24–32° C. to obtain activated stable yeast crystals, separating activated stable yeast crystals by conventional methods followed by incubating novel activated stable yeast crystals in the range of 0.2 to 5% of the volume of the fermentation broth containing molasses having a total reducing sugar concentration in the range of 10–30% and recovering the ethanol from the fermentation broth by known methods.

In an embodiment of the present invention, the growth media used comprises (g/l) malt extract, 1.0–5.0; yeast extract, 1.0–5.0; Peptone, 3.0–10.0 and Molasses, 30.0–50.0.

In an other embodiment of the present invention the yeast used is commercially available Sacchromyces species.

In another embodiment of the present invention, the yeast is cultured by incubating at the temperature of 24–36° C.

In still other embodiment of the present invention, the pH of the growth medium was maintained in the range of 6.0–7.5 during the growth period.

In still another embodiment of the present invention, the yeast is separated by using conventional methods such as centrifugation, settling, decanting the supernatant, etc. from the growth media.

In yet other embodiment of the present invention, the yeast is immobilized using natural polymers selected from sodium alginate, agar-agar, carageenan etc.

In yet another embodiment of the present invention, the immobilized beads are separated from the solution by decanting the salt solution.

In still yet other embodiment of the present invention the immobilized beads are dehydrated by incubating at a preferred dehydrating temperature 24–36° C.

In yet still another embodiment of the present invention, the dehydration is performed for a period ranging between 2–20 hours.

In further embodiment of the present invention, the stable yeast crystals dehydrated until the moisture content in the beads was in the range of 5–30%.

In another embodiment of the present invention, molasses solution having sugar concentration in the range of 3–5% was prepared.

In other embodiment of present invention, the incubation of novel stable yeast crystals is done for a period of 6–48 hours at 24–32° C.

In still another embodiment of the present invention, the activated stable yeast crystals were separated from the activation media by draining out the solution or straining through a mesh or perforated bottoms.

In yet another embodiment of the present invention, the activated stable yeast crystals (0.5–2.0%) in respect of the volume of media were added in conventional manner to fermentation broth which was prepared by diluting the molasses with water to adjust the level of fermentable sugar in the range of 15–30% in the final fermentation broth.

In still other embodiment of the present invention, the reaction was carried out with fermentation media for 18–30 hours at 28±2° C.

In yet other embodiment of the present invention, the activated clustered yeast crystals were separated after fermentation from the fermentation broth by draining out the fermentation broth.

In yet another embodiment of the present invention, the ethanol recovered from the fermented broth is in the range of 7–15%.

According to the process of the invention, the yeast, *Sacchromyces cereviseae*, was grown by inoculation in a growth media consisting of (g/l) malt extract-3.0; yeast extract-3.0; Peptone-5.0 and Molasses-30–50. The media was sterilized at 121° C. for 15 minutes after pH was adjusted to 6.8–7.2 using 1 normal sodium chloride or 1 normal hydrochloric acid. This was then incubated at 28±2° C. on a rotary shaker adjusted with 150 rpm for 24 hours. Large-scale production of yeast was carried out in a fermentor for 24–36 hours with aeration. The yeast was separated by centrifuging the culture broth at 5,000–15,000 rpm for 10 minutes at 24–32° C. The yeast slurry was prepared by mixing the yeast 0.5–10% (w/v) with 0.5–3% (w/v) of natural polymer solution and the immobilized yeast beads were prepared by dropping drop by drop with the help of peristatic pump into the curing (0.05–0.3 M $CaCl_2$) solution. These beads were then cured for overnight at 4° C. in curing solution. The immobilized yeast beads were then separated by decanting the solution and washed with distilled water thoroughly for 2–3 time. After draining the water, the yeast beads were dehydrated at the temperature 24–36° C. for a period of 2–20 hours to obtain stable yeast crystals having a moisture content of 5–30% to obtain stable yeast crystals.

The characteristics of the stable yeast crystals are granular, spherical particles having the diameter 0.3–1.0 mm, dark brown to blackish in colour, hard and robush particles which are insoluble in aqueous or organic medium. These crystals have intrinsic capacity to adsorb and desorb water molecules. These stable yeast crystals were activated by incubating these crystals in the 5–8% molasses solution, consisting of total reducing sugar concentration in the range of 3–5%, at pH 5.0–7.5, for 2–48 hours at temperature 24–32° C. The activated stable yeast crystals were then separated from the solution by draining out the aqueous medium. The fermentation broth was prepared by diluting the molasses with water so that the final solution should contain the fermentable sugars in the range of 10–30% and the pH of the fermentation broth was adjusted to 4.0–4.5. Then 0.5–5.0% activated stable yeast crystals were added to the fermentation broth and incubated for 9–48 hours at 24–40° C. After fermentation the fermented broth separated by decanting and the ethanol was recovered by known methods.

The present invention is explained with the help of the following examples which are illustrative in nature and should therefore be not construed to limit the scope of the present invention.

EXAMPLE 1

Stable Yeast Crystal Preparation:

The yeast was grown using growth media consisting of (g/l) malt extract-3.0; yeast extract-3.0; Peptone-5.0 and Molasses-30–50. The media was sterilized at 121° C. for 15 minutes after pH was adjusted to 6.8–7.2 using 1 normal sodium chloride or 1 normal hydrochloric acid. This was then incubated at 28±2° C. on a rotary shaker adjusted with 150 rpm for 24 hours for growth of yeast. The yeast was separated by centrifugation and the yeast slurry was prepared using 4% (w/v) yeast and 2% (w/v) sodium alginate. The immobilized yeast beads were prepared by dropping this slurry drop by drop in 0.2 M $CaCl_2$ solution and cured in the same solution for overnight at 4° C. The beads were separated by draining the curing solution, and washed thrice with distilled water. The separated immobilized yeast beads were then dehydrated at 28° C. for 12 hours to obtain stable yeast crystals having the moisture content of 5–10%.

EXAMPLE 2

Stable yeast Crystal Preparation:

Using growth media consisting of (g/1) malt extract-3.0; yeast extract-3.0; Peptone-5.0 and Molasses-30–50 the yeast was grown. The media was sterilized at 121° C. for 15 minutes after pH was adjusted to 6.8–7.2 using 1 normal sodium chloride or 1 normal hydrochloric acid before inoculation of yeast. This was then incubated at 28±2° C. on a rotary shaker adjusted with 150 rpm for 24 hours. The yeast was separated by decanting the supernatant after centrifugation and the yeast slurry was prepared using 6% (w/v) yeast and 2% (w/v) sodium alginate. The immobilized yeast beads were prepared by dropping this slurry drop by drop in 0.15 M CaCl$_2$ solution. The beads were separated by draining out the salt solution. The separated immobilized yeast beads were then dehydrated at 28° C. for 4 hours in a rotary evaporator to obtain stable yeast crystals having the moisture content of 5–10%.

EXAMPLE 3

Stable Yeast Crystals Preparation:

Using sterilized growth media, consisting of (g/1) malt extract-3.0; yeast extract-3.0; Peptone-5.0 and Molasses-30–50; pH 6.8–7.2, the yeast was grown. This was then incubated at 28±2° C. on a rotary shaker adjusted with 150 rpm for 24 hours to achieve the maximum growth. The yeast was separated by decanting the supernatant after centrifugation and the yeast slurry was prepared using 10% (w/v) yeast and 1.5% (w/v) sodium alginate. The immobilized yeast beads were prepared by dropping this slurry drop by drop in 0.15 M CaCl$_2$ solution. The beads were separated by draining out the salt solution after 12 hour incubation at 4° C. The separated immobilized yeast beads were then dehydrated at 28° C. for 6 hours in an incubator attached with blower, at 30° C. to obtain stable yeast crystals having the moisture content of 5–10%.

EXAMPLE 4

Ethanol Production Using Activated Stable Yeast Crystals:

Sugar cane molasses was brought from local sugar industry and stored at 4° C. till further use. In 100 ml conical flask, the molasses was diluted with water to adjust the fermentable sugars to 15, 20 and 25%, separately in three different flasks, in a total volume of 100 ml. To this 1.0 gram of activated stable yeast crystals, in each, were added and the flasks were then incubated at 28+2° C. for 24 hours. The activated stable yeast crystals were then separated and the filtrate was used for ethanol recovery. The production of ethanol by using this stable yeast crystals is as follows.

| S. No. | Fermentable sugars In the broth (g/100 ml) (g/100 ml) | Specific gravity of distillate | Percent ethanol produced after 24 hours (ml/100 ml) |
|---|---|---|---|
| 1 | 15.00 | 0.9888 | 7.93 |
| 2 | 20.00 | 0.9849 | 10.97 |
| 3 | 25.00 | 0.9836 | 12.00 |

EXAMPLE 5

Reusability of the Activated Yeast Crystals:

This experiment was planned to find out the reusability of the activated clustered yeast crystals. In 100 ml of conical flask, the molasses was diluted with water to adjust the fermentable sugars to 20% in a total volume of 100 ml. To this 1.0 gram of activated clustered yeast crystals were added and the flask was then incubated at 28+2° C. After 24 hours, the clustered yeast crystals were separated and the fermented broth was used for ethanol recovery. The ethanol produced by using these stable yeast crystals is as follows.

| Batch Number | Fermentable sugars in the broth (g/100 ml) | Percent ethanol produced after 24 hours (ml/100 ml) |
|---|---|---|
| 1 | 20.00 | 10.19 |
| 2 | 20.00 | 10.50 |
| 3 | 20.00 | 10.82 |
| 4 | 20.00 | 10.58 |
| 5 | 20.00 | 09.96 |
| 6 | 20.00 | 10.50 |
| 7 | 20.00 | 10.04 |
| 8 | 20.00 | 09.96 |
| 9 | 20.00 | 10.27 |
| 10 | 20.00 | 10.11 |
| 11 | 20.00 | 10.04 |
| 12 | 20.00 | 10.19 |
| 13 | 20.00 | 10.74 |
| 14 | 20.00 | 09.96 |
| 15 | 20.00 | 10.58 |
| 16 | 20.00 | 10.27 |
| 17 | 20.00 | 10.34 |
| 18 | 20.00 | 10.66 |
| 19 | 20.00 | 10.19 |
| 20 | 20.00 | 10.74 |

EXAMPLE 6

Reusability of the Activated Stable Yeast Crystals:

The same experiment was performed in trial 2 experiment. In 100 ml of conical flask, the molasses was diluted with water to adjust the fermentable sugars to 20% in a total volume of 100 ml. To this 1.0 gram of activated clustered yeast crystals were added and the flask was then incubated at 28+2° C. After 24 hours, the clustered yeast crystals were separated and the fermented broth was used for ethanol recovery. The production of ethanol by using this stable yeast crystals is as follows.

| Batch Number | Fermentable sugars in the broth (g/100 ml) | Percent ethanol produced after 24 hours (ml/100 ml) |
|---|---|---|
| 1 | 20.00 | 10.50 |
| 2 | 20.00 | 10.19 |
| 3 | 20.00 | 10.74 |
| 4 | 20.00 | 10.34 |
| 5 | 20.00 | 10.66 |
| 6 | 20.00 | 10.50 |
| 7 | 20.00 | 10.11 |
| 8 | 20.00 | 09.96 |
| 9 | 20.00 | 10.27 |
| 10 | 20.00 | 10.74 |
| 11 | 20.00 | 10.89 |
| 12 | 20.00 | 10.19 |
| 13 | 20.00 | 10.42 |
| 14 | 20.00 | 09.88 |
| 15 | 20.00 | 10.66 |
| 16 | 20.00 | 10.27 |

-continued

| Batch Number | Fermentable sugars in the broth (g/100 ml) | Percent ethanol produced after 24 hours (ml/100 ml) |
| --- | --- | --- |
| 17 | 20.00 | 10.34 |
| 18 | 20.00 | 10.66 |
| 19 | 20.00 | 10.19 |
| 20 | 20.00 | 10.82 |

The Novelty of the Present Invention has the Following:
1. Dehydration of the immobilized yeast beads at the temperature ranging from 28.32° C.
2. Adjusting the moisture content of the immobilized yeast beads in the range of 5–30% to obtain stable yeast crystals.
3. Activation of the stable yeast crystals by incubating these novel crystals in molasses solution having sugar concentration in the range of 3–5% to obtain activated stable yeast crystals.
4. Reusability of the activated stable yeast crystals for enhanced ethanol production.
5. The activated stable yeast crystals can be used in different bioreactors without any problems associated with free yeast fermentation.
6. The activated stable yeast crystals can be used either in batch fermentation or in continuous fermentation.

Novel Stable Yeast Crystals Prepared According to the Process of the Invention Exhibits the Following Characteristics:
  i. granular in shape.
  ii. dark brown to blackish in colour,
  iii. hard and robust particles,
  iv. insoluble in aqueous or organic medium,
  v. highly stable,
  vi. posses intrinsic capacity to adsorb and desorb water molecules,
  vii. biologically active,
  viii. reusable, and
  ix. non-perishable Ethanol is an important organic solvent and is used as starting compound for production of many organic solvents. In addition, it can replace the natural petroleum sources as energy fields. Alcohol is generally produced by molasses fermentation using care molasses and yeast culture. Conventional method of ethanol production is performed mainly by batch fermentation, which requires addition of fresh yeast for every batch as seed culture and needs maintenance of yeast crystals, thus the process is costly and requires special expertise in microbiology. In this context, the present invention of development of clustered yeast cultures solve the above problems. The fermentation with clustered yeast crystals will result in higher concentration of alcohol in the fermented broth, higher volumetric productivity and increased through put, therefore, reduces the capital expenditure. The clustered yeast crystals are robust, easy to transport, occupy minimum volume, can be used for 15–20 cycles without loss a of activity either in batch or continuous fermentation in different bioreactors and can be stored at room temperature for a prolonged time. Hence, these clustered yeast crystals will cut down the alcohol production expenditure substantially i.e. economic in nature.

The Advantages of this Invention:
1. The prepared stable yeast crystals will reduce substrate and product inhibitions during fermentation.
2. The prepared stable yeast crystals can be stored at room temperature for a prolonged period without the loss of activity.
3. The prepared stable yeast crystals can be reused several times for alcohol production.
4. The prepared stable yeast crystals will facilitate the easy transportation and cheaper packing.
5. The prepared stable yeast crystals can be handled very easily by any unskilled labour.
6. The prepared stable yeast crystals are non-perishable.
7. The prepared stable yeast crystals occupy minimum volume and hence the cells per gram of crystals enhance by several folds.
8. The invented improved ethanol fermentation process with activated stable yeast crystals produces enhanced concentration of ethanol.
9. The invented improved ethanol fermentation process with activated stable yeast crystals yields increased rate of fermentation.
10. The invented improved ethanol fermentation with activated stable yeast crystals can be recycled for 15–20 batches with out the loss of activity.
11. The invented improved ethanol fermentation with activated stable yeast crystals will reduces the cost of fermentation by way of elimination of fresh yeast preparation for every batch.
12. The invented improved ethanol fermentation with activated stable yeast crystals will facilitate easy separation of biocatalyst from the fermented broth.
13. The invented improved ethanol fermentation with activated stable yeast crystals spent wash contains low amount of microbial debris which inturn lowers the Biological Oxygen Demand and Chemical Oxygen Demand.
14. The invented improved ethanol fermentation with activated stable yeast crystals can be produced either in batch fermentation or in continuous fermentation.

What is claimed is:
1. A process for enhancing the production of ethanol comprising:
  (a) culturing yeast Sacchromyces ssp. in a growth medium;
  (b) separating the yeast from the growth medium and immobilizing the yeast using an aqueous natural polymer solution to obtain immobilized yeast beads;
  (c) separating the immobilized yeast beads from the aqueous natural polymer solution and dehydrating the immobilized yeast beads at a temperature ranging from 24–36° C. for a period of 2–20 hours to obtain stable yeast crystals having a moisture content ranging between 5–30%;
  (d) adding the stable yeast crystals to a 5–8% molasses solution and incubating the stable yeast crystals for a period ranging between 6–48 hours at a temperature ranging between 24–32° C. to obtain activated stable yeast crystals; and
  (e) separating the activated stable yeast crystals from the molasses solution by conventional methods, incubating in a fermentation broth the activated stable yeast crystals in an amount between 0.2 to 5% of the volume of the fermentation broth and recovering ethanol from the fermentation broth by known methods; wherein the fermentation broth contains molasses having a total reducing sugar concentration ranging between 10–30%.
2. The process of claim 1 wherein the yeast is a commercially available yeast such as *Sacchromyces cereviceae*.

3. The process of claim 1 wherein the growth medium comprises 1.0–5.0 g/l of malt extract, 1.0–5.0 g/l of yeast extract, 3.0–10.0 g/l of peptone and 30.0–50.0 g/l of molasses.

4. The process of claim 1 wherein the yeast is cultured in step (a) by incubation at a temperature ranging between 24–36° C.

5. The process of claim 1 wherein the growth medium has a pH maintained between 6.0 and 7.5 during step (a).

6. The process of claim 1 wherein the yeast is separated from the growth medium in step (b) by conventional methods selected from the group consisting of centrifugation, settling and decanting.

7. The process of claim 1 wherein the aqueous natural polymer solution is selected from the group consisting of sodium alginate, agar-agar and carageenan.

8. The process of claim 1 wherein the immobilized yeast beads are separated from the solution by decanting the solution.

9. The process of claim 1 wherein the moisture content of the stable yeast crystals is about 5–30%.

10. The process of claim 1 wherein the total reducing sugar concentration of the molasses solution ranges between 3–5%.

11. The process of claim 1 wherein the activated stable yeast crystals are separated in step (e) by draining out the molasses solution or straining through a mesh or perforated bottoms.

12. The process of claim 1 wherein the activated stable yeast crystals are incubated in the fermentation broth for 18–30 hours at 28±2° C.

13. The process of claim 1 further comprising separating the activated stable yeast crystals from the fermentation broth after fermentation in step (e) by draining out the fermentation broth.

14. The process of claim 1 wherein the ethanol recovered from the fermentation broth ranged between 7–15%.

15. Stable yeast crystals prepared according to the process of claim 1 wherein the crystals possess an intrinsic capacity to absorb and desorb water molecules, and are granular in shape; dark brown to blackish in color; hard and robust particles; insoluble in an aqueous or organic medium; highly stable; biologically active; reusable; and non-perishable.

16. A process for preparing stable yeast crystals comprising:

(a) culturing yeast Sacchromyces ssp. in a growth medium;

(b) separating the yeast from the growth medium and immobilizing the yeast using an aqueous natural polymer solution to obtain immobilized yeast beads; and (c) separating the immobilized yeast beads from the aqueous natural polymer solution and dehydrating the immobilized yeast beads at a temperature ranging from 24–36° C. for a period of 2–20 hours to obtain stable yeast crystals having a moisture content ranging between 5–30%.

* * * * *